(12) United States Patent
Niazi

(10) Patent No.: US 9,284,521 B2
(45) Date of Patent: Mar. 15, 2016

(54) PIVOTING PRESSURIZED SINGLE-USE BIOREACTOR

(75) Inventor: Sarfaraz K. Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 118 days.

(21) Appl. No.: 13/429,365

(22) Filed: Mar. 24, 2012

(65) Prior Publication Data

US 2013/0171616 A1   Jul. 4, 2013

(51) Int. Cl.

| | |
|---|---|
| *C12Q 3/00* | (2006.01) |
| *C12M 1/00* | (2006.01) |
| *C12M 3/04* | (2006.01) |
| *C12M 3/06* | (2006.01) |
| *C12M 1/34* | (2006.01) |

(52) U.S. Cl.
CPC .............. *C12M 23/26* (2013.01); *C12M 23/34* (2013.01); *C12M 27/10* (2013.01); *C12M 27/16* (2013.01); *C12M 41/12* (2013.01); *C12M 41/32* (2013.01); *C12M 41/36* (2013.01); *C12M 41/40* (2013.01)

(58) Field of Classification Search
USPC ................................ 435/289.1, 298.1, 298.2
See application file for complete search history.

(56) References Cited

U.S. PATENT DOCUMENTS

| | | | | |
|---|---|---|---|---|
| 6,190,913 | B1 * | 2/2001 | Singh ............................ | 435/394 |
| 8,183,035 | B1 * | 5/2012 | Niazi ................... | B01J 20/2805 435/296.1 |
| 2004/0159616 | A1 | 8/2004 | Cohee et al. | |
| 2005/0272146 | A1 | 12/2005 | Hodge et al. | |
| 2008/0139865 | A1 * | 6/2008 | Galliher et al. ............... | 588/249 |
| 2008/0206862 | A1 * | 8/2008 | Asgari .......................... | 435/325 |
| 2009/0233334 | A1 | 9/2009 | Hildinger et al. | |
| 2010/0009335 | A1 * | 1/2010 | Joseph et al. ...................... | 435/3 |
| 2010/0120136 | A1 * | 5/2010 | Larsen et al. ............... | 435/297.1 |
| 2010/0203624 | A1 | 8/2010 | Singh | |
| 2010/0233775 | A1 * | 9/2010 | Schroder et al. .............. | 435/167 |
| 2011/0033918 | A1 | 2/2011 | Asnaghi et al. | |
| 2012/0018380 | A1 * | 1/2012 | Niazi ................... | B01J 20/2805 210/656 |

FOREIGN PATENT DOCUMENTS

WO        2009042432 A1      4/2009

OTHER PUBLICATIONS

International Search Report and Written Opinion for PCT/US13/33517 dated Jun. 10, 2013.
Supplementary European Search Report dated Sep. 16, 2015, in corresponding EU Application 13 76 9079.

* cited by examiner

*Primary Examiner* — Jill Warden
*Assistant Examiner* — Benjamin Whatley
(74) *Attorney, Agent, or Firm* — Cheryl Liljestrand; Sarfaraz K. Niazi

(57) ABSTRACT

Pressurized hermetically sealed bags disposed inside a cylindrical support and containing a septum with variable density of porosity and dividing the bag into two chambers are used to provide optimal mixing and gasification of nutrient media to grow a variety of biological cultures, particularly the cell cultures to produce a multitude of pharmaceutical and biotechnology products in a disposable system.

5 Claims, 4 Drawing Sheets

PIVOTING PRESSURIZED SINGLE-USE BIOREACTOR

FIELD OF THE INVENTION

The present disclosure relates to pressurized hermetically sealed bags containing products used in the pharmaceutical and biotechnology processing industries and, more particularly, to disposable cell bags or bioreactors.

BACKGROUND OF THE INVENTION

The bioprocessing industry has traditionally used stainless steel systems and piping in manufacturing processes for fermentation and cell culture. These devices are designed to be steam sterilized and reused. Cleaning and sterilization are however costly labor-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last ten years—that of using plastic, single-use disposable bags and tubing, to replace the usual stainless steel tanks.

In particular bioreactors, traditionally made of stainless steel, have been replaced in many applications by disposable bags, which are rocked to provide the necessary aeration and mixing necessary for cell culture. These single-use bags are typically provided sterile and eliminate the costly and time-consuming steps of cleaning and sterilization. The bags are designed to maintain a sterile environment during operation thereby minimizing the risk of contamination.

Commonly used bags are of the "pillow style," mainly because these can be manufactured at low cost by seaming together two flexible sheets of plastic.

One of the successful disposable bioreactor systems uses a rocking table on to which a bioreactor bag is placed. The bioreactor bag is partially filled with liquid nutrient media and the desired cells. The table rocks the bag providing constant movement of the cells in the bag and also aeration from the turbulent air-liquid surface. The bag, typically, has a gas supply tube for the introduction of air or oxygen, and an exhaust gas tube to allow for the removal of respired gases. Nutrients can be added through other tubes.

One possible limitation of this type of device is that it may be difficult to scale up beyond a few hundred liters because poor liquid circulation causes nutrient and waste gradients that inhibit cell performance. This is because the back and forth motion of the single-axis rocker used in these applications creates good liquid circulation in the direction perpendicular to the rocking axis, but relatively little mixing in the direction parallel to the rocking axis. In large volume bags (greater than 100 liters), or in bags with a large length to width ratio, this poor axial circulation can result in a long time to achieve homogeneity of the bag contents. This makes pH control in the bioreactor bag difficult, since additions of acid or base added to the bioreactor to modulate the pH can take a long time to disperse throughout the bag. Nutrients added to the bioreactor bag may not be distributed uniformly. Poor liquid circulation also limits the amount of oxygen that can be transferred from the headspace, and thus the maximum concentration of cells that cannot be cultured.

Circulation flow can be improved by incorporating a second axis of rotation. By synchronizing the two axes it is possible to impart a gyratory motion that greatly improves mixing and mass transfer. However, the addition of second axis increases the cost tremendously, and the increase in mechanical complexity makes the rocker less reliable and more difficult to maintain.

However, all of the above limitations are present in the U.S. Pat. No. 6,190,913 to Vijay Singh (and the resultant Wave Bioreactor marketed by GE Healthcare); as a result, the same inventor proposed in the U.S. patent application Ser. No. 12/676,180 (assigned to GE Healthcare) filed Sep. 15, 2008 to overcome these limitations by creating flexible baffles inside the bag to create a swirling motion in the bag to improve mixing. However, this modification of the existing art does not remove the most significant drawback of producing stress on the seams of the bag that prevent the use of large-scale production using these bags. The proposed modification also does not provide complete mixing as desired from all directions in the bag since the bag is rocked only in one dimension.

Therefore, there is a need for an apparatus that enables a user to scale up the mixing of nutrient media in a bioreactor bag in a flexible container that will assure complete mixing nutrient media from all directions.

SUMMARY OF THE INVENTION

The present invention has been accomplished in view of the above-mentioned technical background, and it is an object of the present invention to provide a bioreactor bag that enables a user to scale up the mixing of nutrient media and efficiently mix the nutrient media in the bioreactor bag.

A bioreactor including a cylindrical support, a flexible container including a septum that defines two chambers in the flexible container with the septum having such variably of porosity that the nutrient media from all sides of the bag passed through the middle of the bag by using a means to pivot the cylindrical support between −110 to +110 degrees; this causes the septum to lift the nutrient media from all sides of the bag and drain it in the middle center of the bag; reversing the cycle in an opposite direction provides the most optimal mixing of the nutrient media. Most efficient movement of nutrient media is observed when the container has been pressurized to form a fixed volume inside so that the bioreactor acts like a hard-walled container yet it retains the advantages of using flexible disposable containers for the manufacturing of biological products.

The container walls and the septum are flexible sheets seamed together. The two outer layers are impermeable while the septum has variable porosity creating a fluid communication between the two chambers. The septum has the highest porosity in the center adjacent to one of the edges. Alternatively, The container may be a modeled structure.

The container is disposed immovably in the cylindrical support such that the septum is vertically aligned and the highest density of pores is in the top middle portion (top vertical and middle horizontal axes). As the cylindrical support is pivoted, the septum sweeps the liquid upwards in the direction of movement of cylindrical support lifting the liquid and pouring it through pores along one side in the center of the septum causing the liquid from all directions of the container to mix uniformly; repeating the operation in opposite direction on a continuous basis produces a highly efficient and uniform mixing of the entire liquid in the container.

Notably absent in the present invention is a means of sparging or introducing a gas in the nutrient media; the mixing of the gas with the nutrient media is achieved through surface intake into nutrient media as it is vigorously turned over repeatedly. While this means of gasification of media is highly suitable for cell culture growth, this may not be sufficient to support growth of bacterial cultures or those cultures requiring very high degree of gasification.

BRIEF DESCRIPTION OF DRAWINGS

These and other advantages of the present invention will become more apparent as the following description is read in conjunction with the accompanying drawings, wherein.

DETAILED DESCRIPTION OF THE PREFERRED EMBODIMENTS

Figure 1A:
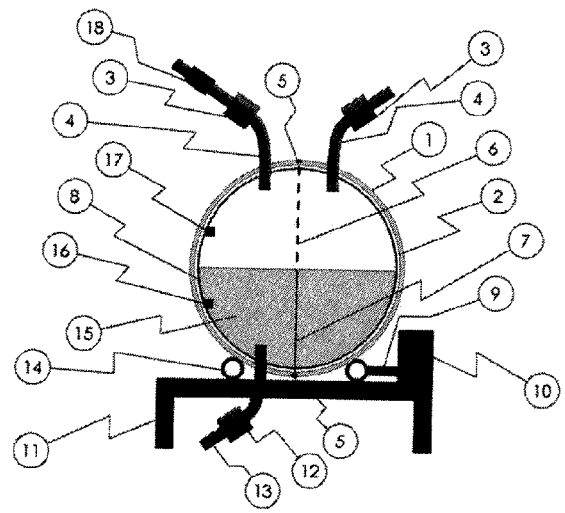
FIG. 1a is the front view a cylindrical support containing a pressurized flexible bag and nutrient media; 1b is a view of the cylindrical support moved clockwise halfway; 1c is a view of the cylindrical support moved clockwise to 110 degrees.

The presently preferred embodiments of the invention are described with reference to the drawings, where like components are identified with the same numerals. The descriptions of the preferred embodiments are exemplary and are not intended to limit the scope of the invention.

A prior art bag is a flat, rectangular, "pillow-style" cell culture bag commonly used in rocking bioreactor applications, for example in the system of U.S. Pat. No. 6,190,913 entitled "Method for Culturing Cells Using Wave-Induced Agitation" filed Aug. 12, 1998. This prior art and other prior art bags are shown in FIG. 1-11 in the U.S. patent application Ser. No. 12/676,180. Another prior art bag is, which is hereby incorporated by reference.

The bag in the present invention (FIG. 1) is formed by seaming together two outer flexible impervious sheets 8 and a perforated septum 7 that has much higher porosity 6 in the center part adjacent to one of the edges forming two chambers capable of holding nutrient media 15 and resulting in an outline seam 5 that goes around the four sides of the bag and forms the point where the flexible bag is attached to the inner surface of the cylindrical support making the bag immovable. Also provided are gas ports 4 attached to sterilizing filters 3 to avoid any contamination from the outside. A liquid port 13 with a sterilizing filter 12 is provided to introduce nutrient media that can also be used to remove liquid from the bag after disconnecting filter 12 and also to introduce a biological culture without the use of the filter. The bag 8 is disposed inside a hard walled cylindrical support 1, which is in turn covered by a heating/cooling element 2. The cylindrical support 1 is supported by a platform 11 through a rolling mechanism 14 that is controlled by a motor 10 through a shall. 9. The pressure of gas in the bag may be controlled by e.g., a valve 18. The pressure can be monitored by a pressure sensor 17. The temperature of the medium can be measured by a temperature sensor 16. A plurality of sensors can be employed for measuring the temperature and pressure at various location in the bag.

Figure 1B:
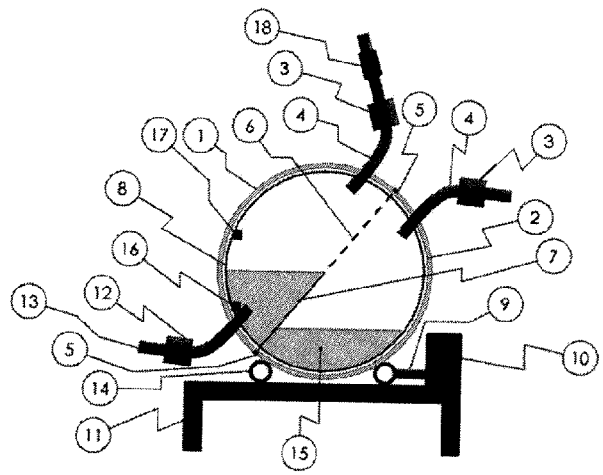
Figure 1C:
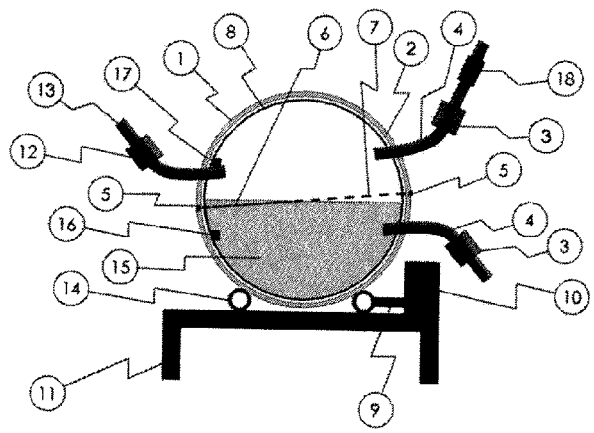

FIG. 1 has three configurations of the invention; FIG. 1a is the starting position wherein the bag 8 is vertically disposed. Nutrient media 15 is introduced in the bag through port 13 and it crosses the septum 7 since it is porous to provide an even level on both sides of the septum 7. It is important to note that the porosity of sheet 8 when disposed vertical in FIG. 1a is much smaller than in the top center portion by at least a factor of ten. The reason for providing porosity throughout the septum is to reduce the pressure on the septum 7 when it is pivoted, allowing it to pass the nutrient media across the two chambers formed by the septum 7. It is further noted that in FIG. 1, the walls of the bag completely line the hard wall of the cylindrical support and this is achieved by introducing a gas through one of the gas ports 4 to pressurize the bag. This also causes the bag to acquire a three-dimensional container. This would generally be desirable when using the invention to grow mammalian cells such as Chines Hamster Ovary cells wherein approximately 5% carbon dioxide mixed in air is provided and the mode of entry of carbon dioxide in the nutrient media is through the surface of the nutrient media.

FIG. 1 shows a clockwise movement of the cylindrical support and FIG. 1b shows the position of the septum 7 when it is pivoted to approximately 30-35 degrees. Note that the septum 7 lifts the nutrient media and when the rotation reaches to above 90 degrees, it drained through the septum mainly through the higher porosity section 6 causing the movement of liquid from the left chamber to the right as shown in FIG. 1. The operation of the cylindrical support is then repeated in an opposite direction to provide mixing from the right chamber to the left chamber and also from back to front. It is noteworthy that as the cylindrical support is pivoted, it is likely that nutrient media leaving one port to exhaust would cover one of the gas ports. Since one of the gas ports is used for introducing gas and the other used as an exhaust, the operation will not be affected regardless of which gas port is temporarily inundated by the nutrient media.

Figure 2:
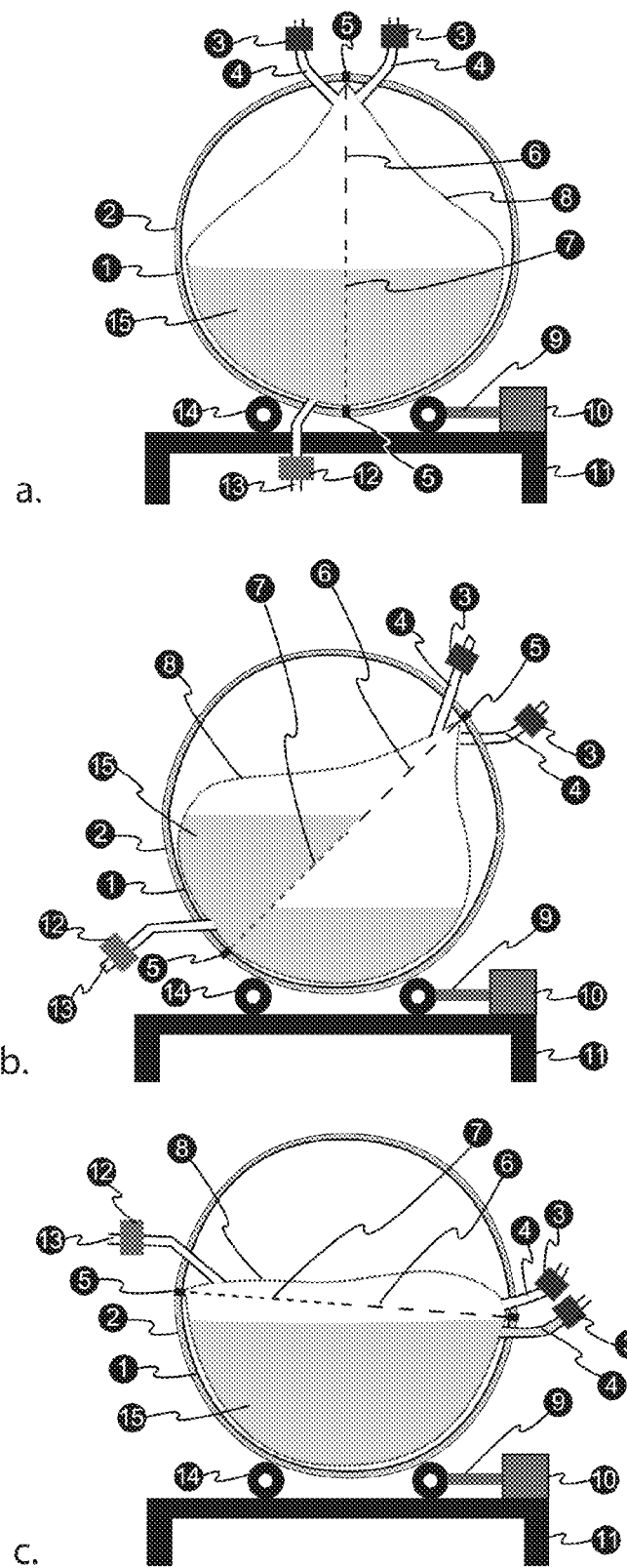
FIG. 2a is a front view a cylindrical support containing an un-pressurized flexible bag and nutrient media; 2b is a front view of the cylindrical support moved clockwise halfway; 2c is a front view of the cylindrical support moved clockwise to 110 degrees.
Figure 3:
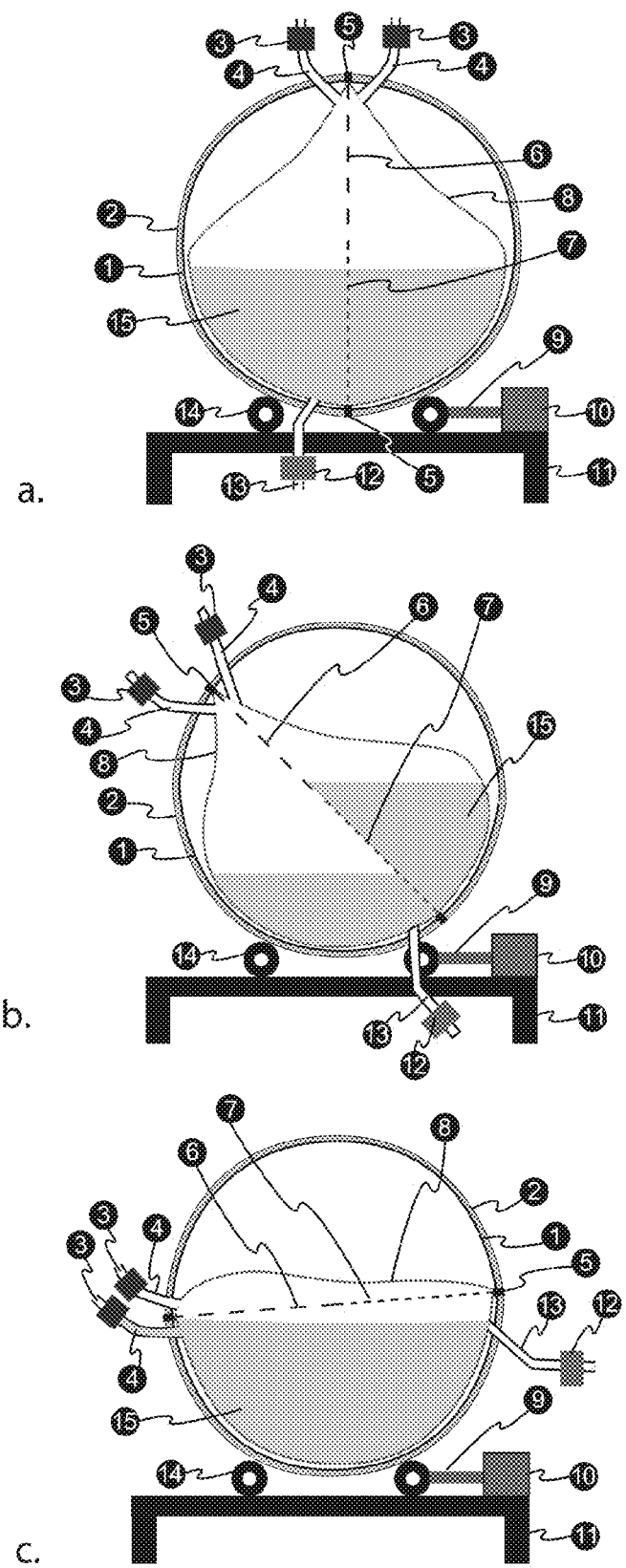
FIG. 3 is a front view a cylindrical support containing an un-pressurized flexible bag and nutrient media; 3b is a front view of the cylindrical support moved clockwise halfway; 3c is a front view of cylindrical support moved counter-clockwise to 110 degrees.
Figure 4:
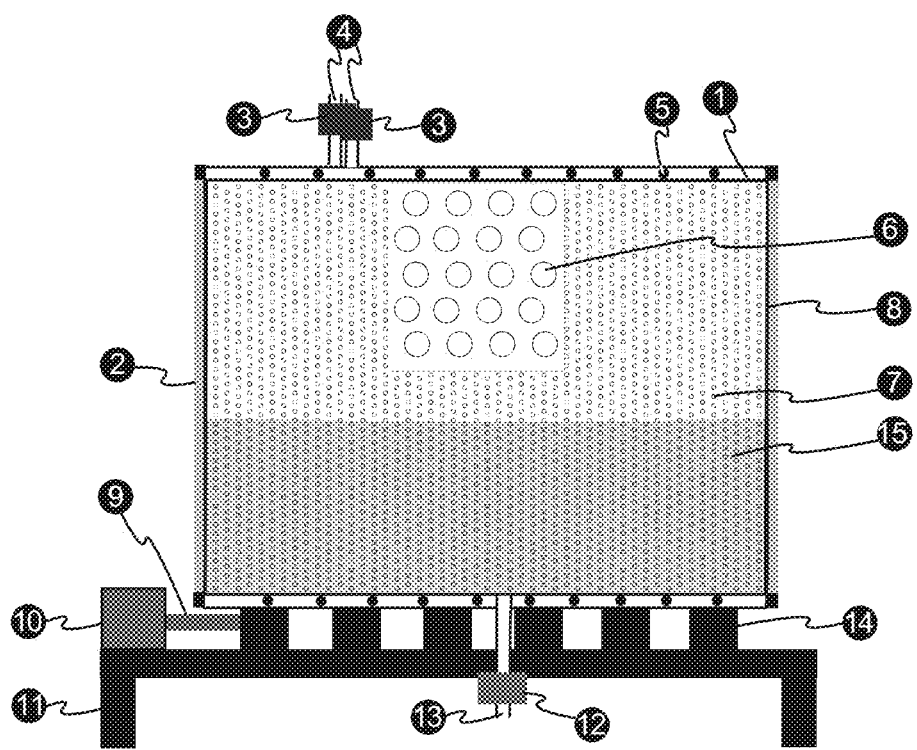
FIG. 4 is a side view of the flexible bag vertically disposed showing the configuration of the pores in the septum.

FIG. 2 shows a side view of the present invention disposed in a starting position showing the septum 7 with its variable perforations 6; it is noteworthy that the largest openings in the septum 7 are provided in the top center position of the septum 7 when vertically disposed in the starting position. This configuration allows the nutrient media to flow from the left to right and also from the back to front as the septum 7 is pivoted lifting the nutrient media.

The bag 7 can be a molded three-dimensional structure or fabricated by seaming flexible sheets. The edges and gusset may be curved seams, or manufactured as a series of straight-line seam segments as shown herein.

This invention provides an apparatus that enables a user to scale up the mixing of nutrient media in a bioreactor bag. This apparatus makes it simple to control the pH where the addition of acid or base to the bioreactor bag does not take a long time to obtain. The uniform mixing from the left to right and from the back to front provides an ideal mixing pattern required for optimal growth of a variety of biological cultures. Thus, this invention provides the user with a simple method to scale up the mixing of nutrient media in a bioreactor bag to provide the highest manufacturing yields of biological products.

The present invention removes all structural and technical hurdles in making use of the technology related to flexible bags being used for large scale bioreactors; a pressurized bag sits within a hard-walled cylindrical support relieving any stress on the seam of the bag and this allows use of construction of bioreactors that can easily contain thousands of liters of nutrient media compared to the prior art that inevitably restricts such volumes to only a few hundred liters.

Although the present bag has been described and illustrated in detail, it is to be clearly understood that this is done by way of illustration and example only and is not to be taken by way of limitation. The scope is to be limited only by the terms of the appended claims.

I claim:

1. A method for producing a biological product comprising:
   a) providing a bioreactor including:
      i) a cylindrical support with an inner surface configured to immovably retain a single-use flexible container with an inner volume and capable of holding nutrient media;
      ii) the single-use flexible container of (a)(i) having at least one interior wall, further including:
         a flexible septum with a surface immovably positioned within the flexible container and defining a right chamber and a left chamber, the septum having a plurality of pores with a variable density over the surface of the septum, wherein diameter of the pores range in size from 1 µm to 1000 µm, and said septum provides fluid communication between the right and the left chambers;
      iii) disposing the flexible container immovably inside the cylinder such that the septum is vertically positioned and a surface comprising 25-30% of the total surface of septum along the middle of the horizontal axis and the middle of the vertical axis has 3-5 times higher density of pores than the rest of the septum;
      iv) at least one liquid inlet;
      v) at least one liquid outlet;
      vi) at least one gas inlet in fluid communication with a source of compressed gas further comprising a sterilizing filter positioned between the source of compressed gas and the container;
      vii) at least one gas outlet capable of controlling the rate of flow of gas;
      viii) at least one sensor to measure the pressure inside the flexible container;
      ix) at least one sensor to measure the temperature of the liquids in the flexible container;
      x) a heater and/or a cooling element for heating and/or cooling the flexible container;
      xi) a motor driving a shaft connected to a rolling mechanism for pivoting the cylindrical support along its circular axis between −110 to +110 degrees;
   b) disposing the flexible container in the cylindrical support and immovably fixing the flexible container to the inner surface of the cylindrical support;
   c) introducing the nutrient media in the flexible container through the liquid inlet;
   d) introducing a biological culture capable of growing in the nutrient media and producing a biological product in the flexible container through the liquid inlet;
   e) heating or cooling the nutrient media to a pre-determined temperature;
   f) connecting the gas inlet to a source of a compressed gas;
   g) starting the flow of the compressed gas with sufficient pressure to achieve a pre-determined pressure in the flexible container that causes the flexible container to expand and stay in continuous contact with the inner surface of the cylindrical support;
   h) continuing the flow of compressed gas to maintain the pre-determined pressure in the flexible container;
   i) moving the shaft to pivot the cylindrical support between the angles from −110 and +110 degrees at a pre-determined frequency;
   j) monitoring the density and the viability of the biological culture in the nutrient media at predetermined time intervals;
   k) monitoring the concentration of the biological product in the nutrient media at predetermined time intervals;
   l) stopping the pivoting of the cylindrical support when the density of the biological culture or the concentration of the biological product reaches a pre-determined level and removing the nutrient media from the flexible container for further processing of the purification of the biological product in the nutrient media.

2. The method for producing a biological product according to claim 1, wherein the flexible container is substantially cylindrical, ovoid, cuboid, round, rectangular or square in shape.

3. The method for producing a biological product according to claim 1, wherein the flexible container is generally a pillow-type flexible bag, wherein at least the internal portion of the flexible container and the septum is comprised of a biocompatible material.

4. The method for producing a biological product according to claim 1, wherein the container further comprises a plurality of sensors.

5. The method for producing a biological product according to claim 1, wherein the biological culture comprises bacteria, yeast, baculoviruses, mammalian cells or plant cells.

* * * * *